United States Patent
Ghone et al.

(10) Patent No.: US 12,173,013 B2
(45) Date of Patent: *Dec. 24, 2024

(54) SYNTHETIC PROCESSES AND SYNTHETIC INTERMEDIATES

(71) Applicant: TAXIS PHARMACEUTICALS, INC., Monmouth Junction, NJ (US)

(72) Inventors: Sanjeevani Ghone, Monmouth Junction, NJ (US); Fu-An Kang, Monmouth Junction, NJ (US); Nareshkumar Jain, Monmouth Junction, NJ (US); Ajit K. Parhi, Monmouth Junction, NJ (US); Ravi Ponnaiah, Hyderabad (IN); Anil Kumar Soni, Hyderabad (IN); Siva Rami Reddy Athunuri, Hyderabad (IN); Thrisulapani Korrakuti, Hyderabad (IN); Pullarao Seelam, Hyderabad (IN)

(73) Assignee: Taxis Pharmaceuticals, Inc., Monmouth Junction, NJ (US)

( * ) Notice: Subject to any disclaimer, the term of this patent is extended or adjusted under 35 U.S.C. 154(b) by 136 days.

This patent is subject to a terminal disclaimer.

(21) Appl. No.: 18/104,013

(22) Filed: Jan. 31, 2023

(65) Prior Publication Data

US 2023/0257397 A1  Aug. 17, 2023

Related U.S. Application Data

(63) Continuation of application No. 16/997,716, filed on Aug. 19, 2020, now abandoned, which is a continuation of application No. 16/498,870, filed as application No. PCT/US2018/025502 on Mar. 30, 2018, now Pat. No. 10,774,093.

(30) Foreign Application Priority Data

Mar. 30, 2017  (IN) ............................. 201741011533

(51) Int. Cl.
C07D 513/04 (2006.01)
B01J 23/44 (2006.01)

(52) U.S. Cl.
CPC ............ C07D 513/04 (2013.01); B01J 23/44 (2013.01)

(58) Field of Classification Search
None
See application file for complete search history.

(56) References Cited

U.S. PATENT DOCUMENTS

| | | |
|---|---|---|
| 4,309,539 A | 1/1982 | Boller et al. |
| 4,782,058 A | 11/1988 | Griffith |
| 4,826,990 A | 5/1989 | Musser et al. |
| 5,077,142 A | 12/1991 | Sakon et al. |
| 5,177,067 A | 1/1993 | Guerry et al. |
| 5,177,075 A | 1/1993 | Suto et al. |
| 6,348,482 B1 | 2/2002 | Hammond |
| 6,515,010 B1 | 2/2003 | Franchini et al. |
| 8,088,791 B2 | 1/2012 | Brown et al. |
| 8,415,383 B2 | 4/2013 | Haydon et al. |
| 8,492,414 B2 | 7/2013 | Haydon et al. |
| 8,865,736 B2 | 10/2014 | Brown et al. |
| 8,933,096 B2 | 1/2015 | Lavoie et al. |
| 9,458,150 B2 | 10/2016 | Lavoie et al. |
| 10,071,082 B2 | 9/2018 | Lavoie et al. |
| 10,513,528 B2 | 12/2019 | Ponnaiah et al. |
| 10,774,093 B2 | 9/2020 | Ghone et al. |
| 2002/0035090 A1 | 3/2002 | Zeldis et al. |
| 2002/0040147 A1 | 4/2002 | Hammond et al. |
| 2002/0055516 A1 | 5/2002 | Miyazaki et al. |
| 2002/0077333 A1 | 6/2002 | Dey et al. |
| 2003/0181519 A1 | 9/2003 | Mewshaw et al. |
| 2005/0043300 A1 | 2/2005 | Middleton et al. |

(Continued)

FOREIGN PATENT DOCUMENTS

| | | |
|---|---|---|
| CN | 101404989 A | 4/2009 |
| DE | 4327748 A1 | 2/1995 |

(Continued)

OTHER PUBLICATIONS

Akiba, et al., "Preparation of 13-Substituted 8H-Dibenzo[a,g]quinolizin-8-onces by Intramolecular Wittig-Horner Reaction of Dialkyl 2-(o-Acyl-benzoyl)-1,2-dihydro-1-isoquinolylphosphonates", Bull. Chem. Soc. Japan, 57 (8), 2199-2192 (1984).

(Continued)

*Primary Examiner* — Zinna Northington Davis
(74) *Attorney, Agent, or Firm* — Viksnins Harris Padys Malen LLP

(57) ABSTRACT

The invention provides synthetic intermediates and synthetic processes that are useful for preparing the antibacterial agent TXA709:

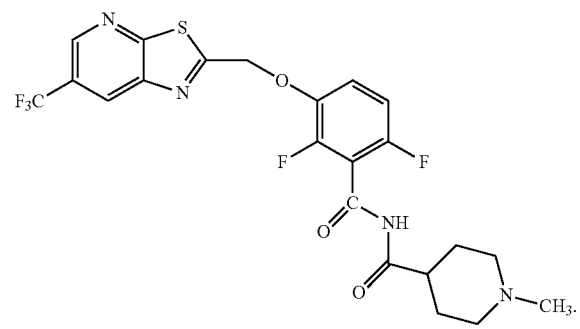

TXA709

16 Claims, 4 Drawing Sheets

(56) References Cited

U.S. PATENT DOCUMENTS

| | | |
|---|---|---|
| 2006/0183943 A1 | 8/2006 | Hu |
| 2008/0027028 A1 | 1/2008 | Chichak |
| 2008/0300239 A1 | 12/2008 | Adams et al. |
| 2009/0076074 A1 | 3/2009 | Jung et al. |
| 2009/0312319 A1 | 12/2009 | Ren et al. |
| 2010/0120810 A1 | 5/2010 | Leblond et al. |
| 2010/0173933 A1 | 7/2010 | Brown et al. |
| 2012/0022061 A1 | 1/2012 | Lavoie |
| 2012/0196891 A1 | 8/2012 | Iwakoshi |
| 2013/0109713 A1 | 5/2013 | Lavoie et al. |
| 2013/0116278 A1 | 5/2013 | Lavoie |
| 2014/0135332 A1 | 5/2014 | Haydon et al. |
| 2014/0350024 A1 | 11/2014 | Lavoie et al. |
| 2015/0011559 A1 | 1/2015 | Lavoie et al. |
| 2015/0031694 A1 | 1/2015 | Lavoie et al. |
| 2015/0133465 A1 | 5/2015 | Lavoie et al. |
| 2015/0307517 A1 | 10/2015 | Lavoie et al. |
| 2016/0367531 A1 | 12/2016 | Lavoie et al. |
| 2018/0179225 A1 | 6/2018 | Lavoie et al. |
| 2018/0338957 A1 | 11/2018 | Lavoie et al. |
| 2021/0139508 A1 | 5/2021 | Ghone et al. |

FOREIGN PATENT DOCUMENTS

| | | |
|---|---|---|
| EP | 0136745 A2 | 4/1985 |
| EP | 0719764 A1 | 7/1996 |
| EP | 1078920 A1 | 2/2001 |
| EP | 1724262 A1 | 11/2006 |
| JP | 2012051885 A | 3/2012 |
| WO | 1992019242 A1 | 11/1992 |
| WO | 2002044127 A1 | 6/2002 |
| WO | 2003018017 A1 | 3/2003 |
| WO | 2003078397 A1 | 9/2003 |
| WO | 2003099274 A1 | 12/2003 |
| WO | 2004000814 A1 | 12/2003 |
| WO | 2004005472 A2 | 1/2004 |
| WO | 2004018414 A1 | 3/2004 |
| WO | 2004041210 A2 | 5/2004 |
| WO | 2004073709 A1 | 9/2004 |
| WO | 2004087145 A2 | 10/2004 |
| WO | 2005075428 A1 | 8/2005 |
| WO | 2005097100 A2 | 10/2005 |
| WO | 2006067048 A1 | 6/2006 |
| WO | 2006105289 A1 | 10/2006 |
| WO | 2007002325 A1 | 1/2007 |
| WO | 2007107758 A1 | 9/2007 |
| WO | 2007148093 A1 | 12/2007 |
| WO | 2008016596 A2 | 2/2008 |
| WO | 2009037485 A1 | 3/2009 |
| WO | 2009040507 A1 | 4/2009 |
| WO | 2009074810 A1 | 6/2009 |
| WO | 2009074812 A1 | 6/2009 |
| WO | 2009081892 A1 | 7/2009 |
| WO | 2010127307 A1 | 11/2010 |
| WO | 2011112435 A1 | 9/2011 |
| WO | 2011156626 A1 | 12/2011 |
| WO | 2012142671 A1 | 10/2012 |
| WO | 2013142712 A1 | 9/2013 |
| WO | 2014074932 A1 | 5/2014 |
| WO | 2017147316 A1 | 8/2017 |

OTHER PUBLICATIONS

Augstein, et al., "Synthesis of 11-Hydroxy-2,3,9, 10-tetramethoxy-May 6, 13,13a-tetrahydro-8H-dibenzo[a,g]quinolizine. A Contribution of the Structure of Stepharotine", Stepharotine, vol. 34, No. 5, 3149-1352 (1969).
Bayer, et al., "Pyridyl-substituierte Tetralonderivate: Eine neue Klasse nichtsteroidaler Aromatase-Inhibitoren", Arch. Pharm. 324, 815-820 (1991). [English Abstract].
Bedi, et al., "Synthesis and biological activity of novel antibacterial quinazolines", Bioorganic & Medical Chemistry Letters 14, 5211-5213 (2004).
Beilstein, Database Beilstein Institute for Organic Chemistry, XP002591900, Database Accession No. 3837583 (BNR) abstract (1930).
Beilstein, Database Beilstein Institute for Organic Chemistry, XP002591901, Database Accession No. 3834367 (BRN) abstract (1918).
Beuria, T.K., et al., "Sanguinarine Blocks Cytokinesis in Bacteria by Inhibiting FtsZ Assembly and Bundling", Biochemistry, 44, 16584-16593 (2005).
Bild, et al., "Discovery of Inhibitors of MCF-7 Tumor Cell Adhesion to Endothelial Cells and Investigation on their Mode of Action", Arch. Pharm. Pharm. Med. Chem., 337, 687-694 (2004).
Chemical Abstracts, STN Registry Database Record for RN 338394-05-1, Entered May 25, 2001.
Chemical Abstracts Database, RN 1375188-04-7 for N-(Methylsulfonyl)-3-[(2-methyl-4-thiazolyl)methoxy]-Benzamide, 1 page, (Entered Jun. 5, 2012).
Chen, et al., "Synthesis and Antibacterial Evaluation of Certain Quinolone Derivatives", J. Med. Chem. 44, 2374-2377 (2001).
Cole, et al., "Potential Tumor-Selective Nitroimidazolylmethyluracil Prodrug Derivatives: Inhibitors of the Angiogenic Enzyme Thymidine Phosphorylase", J. Med. Chem. 46, 207-209 (2003).
Czaplewski, L, et al., "Antibacterial alkoxybenzamide inhibitors of the essential bacterial cell division protein FtsZ", Bioorganic & Medicinal Chemistry Letters 19, 524-527 (2009).
Database Registry, Chemical Abstracts Service, Registry No. 1211090-40-2, entered Mar. 17, 2010.
Database Registry, Chemical Abstracts Service, Registry Nos. 1177870-80-2, entered Aug. 30, 2009; 1024284-46-5, entered Jun. 1, 2008; 1022864-66-9, entered May 27, 2008; 1022446-60-1, 1022368-26-8, entered May 25, 2008; 1022127-38-3 entered May 23, 2008.
Database Registry, RN 1421604-28-5, 1 page (Feb. 21, 2013).
Database Registry, RN 1823143-25-4, 1 page (Dec. 4, 2015).
Database Registry [Online], Chemical Abstracts Service, XP002570845, Database accession No. 1043564-34-0/RN, abstract (2008).
Denes, et al., "The chemistry of sanguinarine", XP002570844, Chemical Abstracts Service, Database accession No. 1960:91836, abstract, Magyar Kemiai Folyoirat, 64, 125-130 (1958).
Dorwald, F., "Side Reactions in Organic Synthesis: A Guide to Successful Synthesis Design", Wiley-VCH Verlag GmbH & Co. KGaA, Wienheim, 32 pages (2005).
Dyke, et al., "The Chemistry of Cryptopine-I The Epicryptopines", Tetrahedron, vol. 24, No. 3, 1455-1465 (1968).
Dyke, et al., "The Chemistry of Cryptopine-II The Pseudocryptopine Chloride", Tetrahedron, vol. 25, 5375-5381 (1969).
Dykhuizen, "Santa Rosalia revisited: Why are there so many species of Bacteria?", Antoine van Leeuwenhock, 73, 25-33 (1998).
Elsen, N, et al., "Mechanism of Action of the Cell-Division Inhibitor PC190723: Modulation of FtsZ Assembly Cooperativity", Journal of American Chemical Society 134, 12342-12345 (2012).
Foroumadi, et al., "Synthesis and in vitro antibacterial evaluation of N-[5-(5-nitro-2-thienyl)-1,3,4-thiadiazole-2-yl]piperazinyl quinolones", European Journal of Medicinal Chemistry, 38, 851-854 (2003).
Gopinath, et al., "Dehydrogenation cyclization of 2-aryl-I-tetralone oxime acetates", XP002570843, Chemical Abstracts Service, Database accession No. 1960:23123, abstract, Current Science, 28, 241-242 (1959).
Haydon, et al., "Creating an antibacterial with in vivo efficacy: synthesis and characterization of potent inhibitors of the bacterial cell division protein FtsZ with improved pharmaceutical properties", J. Med. Chem 53, 3927-3936 (2010).
Huecas, et al., "Protein Structure and Folding: The Interactions of Cell Division Protein FtsZ with Guanine Nucleotides", J. Biol. Chem. 282, 37515-37528 (2007).
Huttunen, et al., "Prodrugs—An Efficient Way to Breach Delivery and Targeting Barriers", Current Topics in Medicinal Chemistry, 11, 2265-2287 (2011).
Ishii, et al., "Studies on the Chemical Constituents of Rutaceous Plants. LV. 1. The Development of a Versatile Method for the Synthesis of Antitumor-Active Benzo[c]phenanthridine Alkaloids.

(56) References Cited

OTHER PUBLICATIONS (5)1. A New Method for Quaternization of the Benzo[c]phenanthridine Nucleus", Chem. Pharm. Bull., 32(8), 2984-2994 (1984).
Ito, et al., "A medium-term rat liver bioassay for rapid in vivo detection of carcinogenic potential of chemicals", Cancer Sci, vol. 94 (1), 3-8 (2003).
Jackson, et al., "Non-Steroidal Aromatase Inhibitors Based on a Biphenyl Scaffold: Synthesis, in vitro SAR, and Molecular Modelling", Chem Med Chem 3, 603-618 (2008).
Jaiswal, et al., "Totarol inhibits bacterial cytokinesis by perturbing the assembly dynamics of FtsZ", Biochemistry, vol. 46(14), 4211-4220 (2007).
Kaul, et al., "A Bactericidal Guanidinomethyl Biaryl That Alters the Dynamics of Bacterial FtsZ Polymerization", Journal of Medicinal Chemistry, 55, 10160-10176 (2012).
Kaul, M., et al., "A FtsZ-Targeting Benzamide Prodrug with Improved Pharmacokinetics and Enhanced In Vivo Efficacy against Methicillin-Resistant *Staphylococcus aureus*", Antimicrobial Agents and Chemotherapy 59, 1-9 (2015).
Kaul, M, et al., "An FtsZ-Targeting Prodrug with Oral Antistaphylococcal Efficacy In Vivo", Antimicrobial Agents and Chemotherapy 57(12), 5860-5869 (2013).
Kaul, Malvika, et al., "Enterococcal and streptococcal resistance to PC190723 and related coumpounds: Molecular insights from a FtsZ mutational analysis", Biochimie 95, 1880-1887 (2013).
Kaul, M., et al., "Pharmacokinetics and in vivo antistaphylococcal efficacy of TXY 541, a 1-methylpiperidine-4-carboxamide prodrug of PC190723", Biochemical Pharmacology 86, 1699-1707 (2013).
Kaul, M, et al., "TXA709, an FtsZ-Targeting Benzamide Prodrug with Improved Pharmacokinetics and Enhanced In Vivo Efficacy against Methicillin-Resistant *Staphylococcus aureus*", Antimicrobial Agents and Chemotherapy 59 (8), 4845-4855 (2015).
Lee, M, et al., "Quantification of Small Molecule-Protein Interactions using FRET between Tryptophan and the Pacific Blue Fluorophore", ACS Omega 1, 1266-1276 (2016).
Leroux, et al., "N-(4-Biphenylmethyl)imidazoles as Potential Therapeutics for the Treatment of Prostate Cancer: Metabolic Robustness Due to Fluorine Substitution?", Helvetica Chimica Acta, vol. 86, 2671-2686 (2003).
Moellering, R, "MRSA: the first half century", J Antimicrob Chemother 67, 4-11 (2012). Advance Access publication Oct. 2011.
Musser, J, et al., "N-[(Arylmethoxy)phenyl] Carboxylic Acids, Hydroxamic Acids, Tetrazoles, and Sulfonyl Carboxamides. Potent Orally Active Leukotriene D, Antagonists of Novel Structure", J. Med. Chem. vol. 33, 240-245 (1990).
Nicolson, et al., "Potentiation of methicillin activity against methicillin-resistant *Staphylococcus aureus* by diterpenes", FEMS Microbiology Letters 179, 233-239 (1999).
Okudaira, et al., "A Study of the Intestinal Absorption of an Ester-Type Prodrug, ME3229, in Rats: Active Efflux Transport as a Cause of Poor Bioavailability of the Active Drug", Journal of Pharmacology and Experimental Therapeutics, vol. 294(2), 580-587 (2000).
Online: , http://web.archive.org/web/20070630171813/http://www.enamine.net/index.php?option=com_content&task=view&id=22&menuid=51&PHPSESSID=64a4f248f69d671a413f487bb62c4d90, dated Jun. 30, 2007, 1 page, accessed Apr. 1, 2015.
Patent Cooperation Treaty, International Searching Authority, Search Report and Written Opinion for PCT/US2018/025502, 10 pages, Jun. 27, 2018.
Pitt, W, et al., "Heteroaromatic Rings of the Future", J. Med. Chem. 52, 2952-2963 (2009).
Pozharskii, A. F., et al., "Heterocycles in Life and Society. An Introduction to Heterocyclic Chemistry and Biochemistry and the Role of Heterocycles in Science, Technology, Medicine and Agriculture", Wiley, pp. 1-6 (1997).
Pubchem, "RZDCCEMQGPEORD-UHFFFAOYSA-O", Compound Summary for CID 69980720, 12 pages (Create Date Dec. 1, 2012).
Qiang, S., et al., "Synthesis and Biological Evaluation of Novel FtsZ targeted 3-arylalkoxy-2,6-difluorobenzamides as Potential Antimicrobial Agents", Chemical Biology & Drug Design 87(2), 257-264 (2016).
Roesch, et al., "Synthesis of isoquinolines and pyridines by the palladium-catalyzed iminoannulation of internal alkynes", J. Org. Chem. 66, 8042-8051 (2001).
Sanders, et al., "Selective Cytotoxicity of Topoisomerase-Directed Protoberberines against Glioblastoma Cells", Biochemical Pharmacology, vol. 56, 1157-1166 (1998).
Schonenberger, "Synthesis and Pharmacological test of N-(3'-Methoxy-benzamidomethyl)-D-norephedrine and Analogous Compounds", Arch. Pharm 309, 289-301 (1976). [English Abstract].
Sethi, et al., "Enzyme Inhibition VIII: Mode of Inhibition of Reverse Transcriptase Activity of Analogues, Isomers, and Related Alkaloids of Coralyne", Journal of Pharmaceutical Sciences, vol. 74 (8), 889-891 (1985).
Shaheen, B, et al., "A microbial aetiology of acne: what is the evidence?", British Journal of Dermatology 165, 474-485 (2011).
Silverman, R, "The Organic Chemistry of Drug Design and Drug Action", 2nd Edition, pp. 17-23 (2008).
Singh, J, et al., "Structure-Activity Relationship Studies Leading to the Identification of (2E)-3-[I-[(2,4-Dichlorophenyl)methyl]-5-fluoro-3-methyl-IH-indol-7-yl]-N-[(4,5-dicholoro-2-thienyl)sulfonyl]-2-propenamide (DG-041), a Potent and Selective Prostanoid EP3 Receptor", J. Med. Chem. 53, 18-36 (2010).
Wachall, et al., "Imidazole Substituted Biphenyls: A New Class of Highly Potent and In Vivo Active Inhibitors of P450 17 as Potential Therapeutics for Treatment of Prostate Cancer", Bioorganic and Medical Chemistry 7, 1913-1924 (1999).
Wigbers, et al., "Synthesis, Structures, and Aggregation Properties of N-Acylamidines", Eur. J. Org. Chem., 861-877 (2011).
Wu, et al., "Regulatory perspectives of Type II prodrug development and time-dependant toxicity management: Nonclinical Pharm/Tox analysis and the role of comparitive toxicology", Toxicology 236, 1-6 (2007).
Yaeko, et al., "Studies on the Constituents of Bocconia Cordata. IV. Transformation of sanguinarine into bocconine", XP002570841, Chemical Abstracts Service, Database accession No. 1992:129332, abstract, Journal of Heterocyclic Chemistry, 28(8), 1841-1843 (1991).
Yamaguchi, et al., "Utilization of Protopine and Related Alkaloids. XIV. Oxidation of the Photo-adduct of 1-Oxoanhydromethylberberine with Nitrosobenzene, and Synthesis of Ring C-Substituted Benzo[c]phenanthridines", Chem. Pharm. Bull., 31(5), 1601-1611 (1983).

SYNTHETIC PROCESSES AND SYNTHETIC INTERMEDIATES

PRIORITY APPLICATION

This application is a continuation of U.S. patent application Ser. No. 16/997,716 filed Aug. 19, 2020, which is a continuation of U.S. patent application Ser. No. 16/498,870 filed Sep. 27, 2019, which issued as U.S. Pat. No. 10,774,093 on Sep. 15, 2020, which is a 35 U.S.C. § 371 National Stage application of International Application No. PCT/US2018/025502 filed Mar. 30, 2018, which claims priority to Indian Provisional Application No. 201741011533 that was filed Mar. 30, 2017. The entire content of the applications referenced above are hereby incorporated by reference herein.

BACKGROUND

International Patent Application Publication Number WO 2014/074932 describes compounds of formula (I):

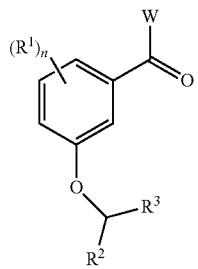

(I)

that are useful as antimicrobial agents. One of these compounds TXA709:

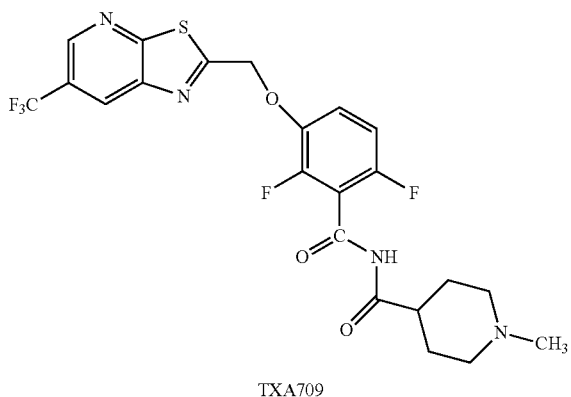

TXA709 has been selected for clinical development as an antibacterial agent.

Currently there is a need for improved synthetic processes and synthetic intermediates that can be used to prepare TXA709 in higher yield on a commercial (e.g. kg) scale.

SUMMARY

The invention provides synthetic processes and synthetic intermediates that can be used to prepare TXA709 in higher yield on a commercial (e.g. kg) scale.

Accordingly, one embodiment provides a compound of formula 9:

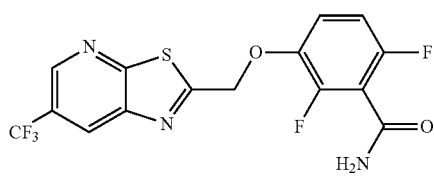

9 or a salt thereof.

Another embodiment provides a salt of formula 11:

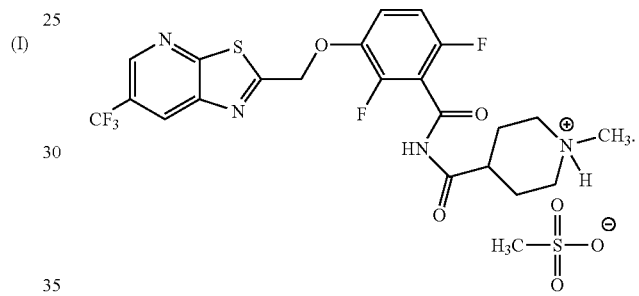

11

Another embodiment provides a process for preparing a compound of formula 8:

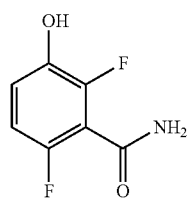

8 comprising converting a compound of formula 7:

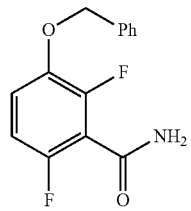

7 to the compound of formula 8.

Another embodiment provides a process for preparing TXA709, comprising converting an amide of formula 9:

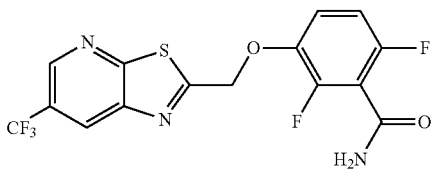

to TXA709.

Another embodiment provides a process for preparing a compound of formula 9:

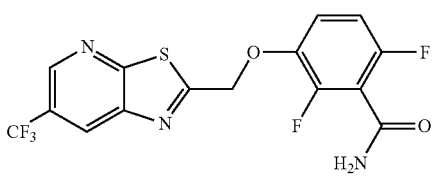

comprising reacting a compound of formula 3:

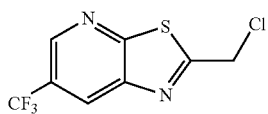

with a compound of formula 8:

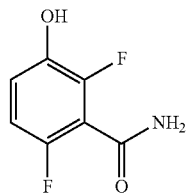

to provide the compound of formula 9.

Another embodiment provides a process for preparing a salt of formula 11:

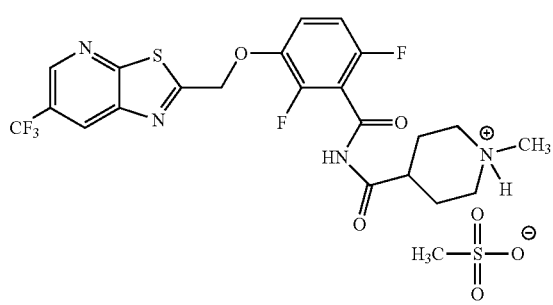

comprising converting TXA709 to the salt of formula 11.

DETAILED DESCRIPTION

Figure 1:
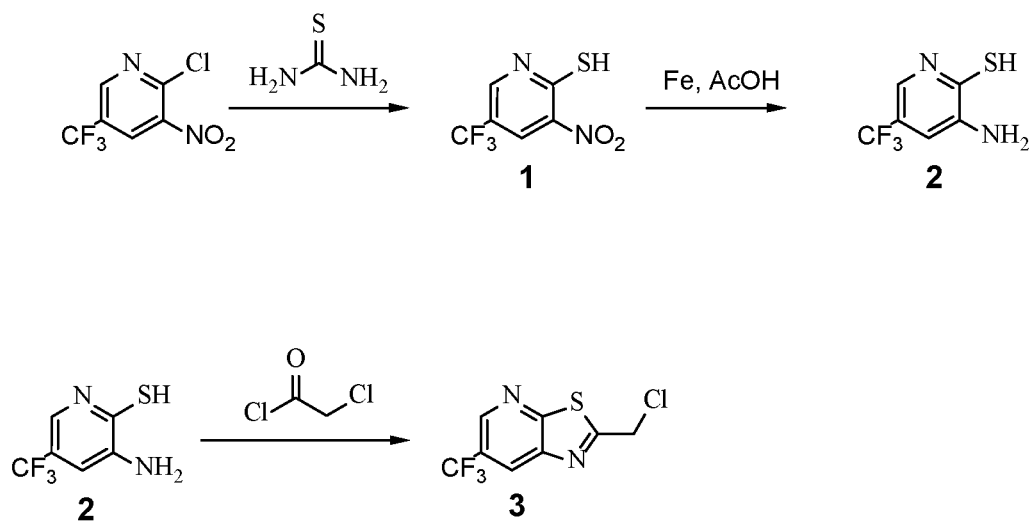
FIG. 1 illustrates the preparation of synthetic intermediate 3.
Figure 2:
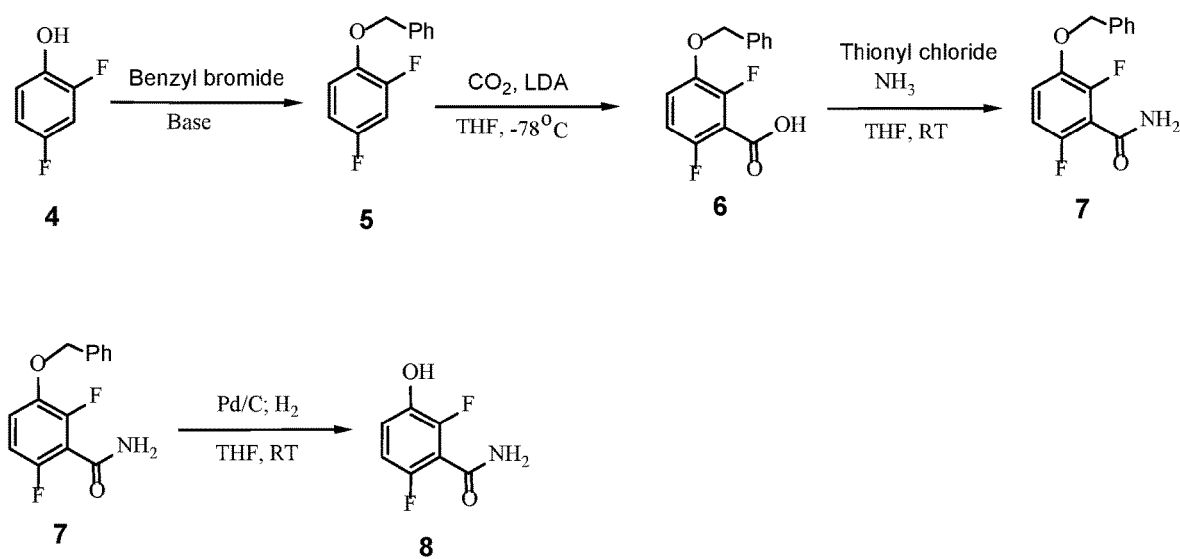
FIG. 2 illustrates the preparation of synthetic intermediate 8.
Figure 3:
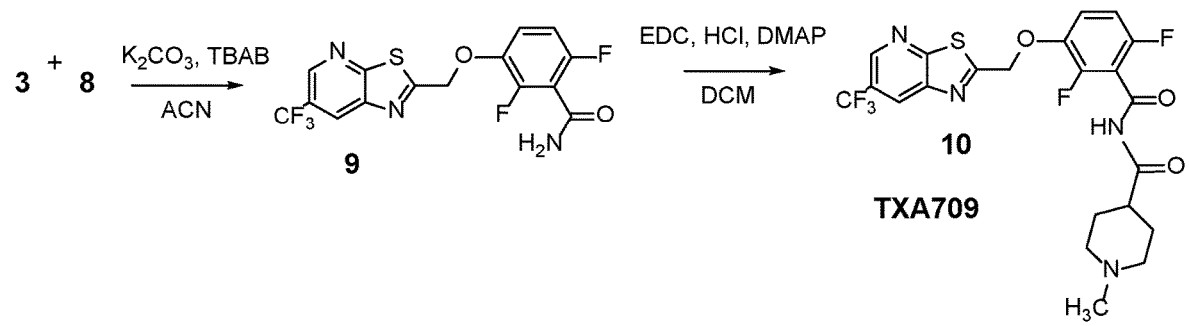
FIG. 3 illustrates the preparation of TXA709 from synthetic intermediates 3 and 8.
Figure 4:
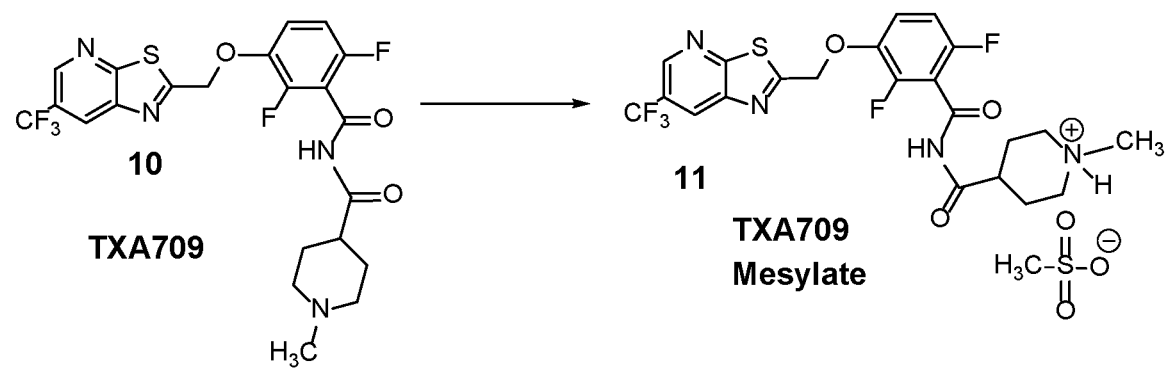
FIG. 4 illustrates the preparation of salt 10.

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents.

In one embodiment the invention provides a process for preparing a compound of formula 8:

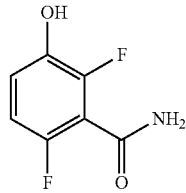

8 comprising converting a compound of formula 7:

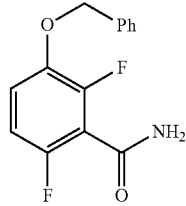

7 to the compound of formula 8. In one embodiment the conversion can be carried out by hydrogenation. In one embodiment the hydrogenation can be carried out in a polar solvent, such as, for example, a solvent that comprises methanol, ethanol, or ethyl acetate. In one embodiment the hydrogenation can be carried out using a catalyst that comprises a metal, such as, for example, palladium on carbon. In one embodiment the hydrogenation can be carried out in a non-polar solvent, such as, for example, a solvent that comprises benzene, tetrahydrofuran, or touene. In one embodiment the conversion can be carries out at a temperature in the range from about −78° C. to about 65° C.

In one embodiment the invention provides a process for preparing TXA709, comprising converting an amide of formula 9:

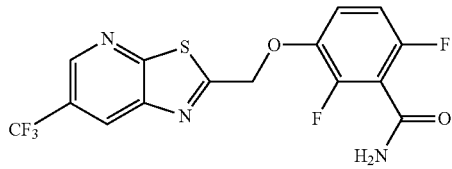

9 to TXA 709. In one embodiment the conversion can be carried out in a polar solvent, such as, for example, a solvent that comprises dichloromethane DCM, dimethylformamide DMF, or dichloroethane DCE. In one embodiment the conversion is carried out at temperature in the range of from about 0° C. to about 40° C. In one embodiment the conversion is carried out at temperature in the range of from about 35 to about 40° C. in dichloromethane with EDC·HCl/DMAP system as coupling agent.

In one embodiment the invention provides a process for preparing an amide of formula 9:

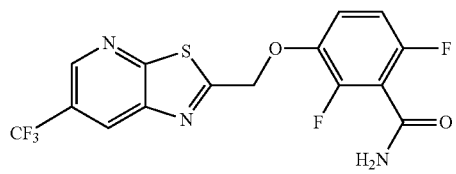

9 by reacting a compound of formula 3:

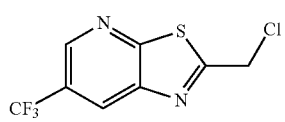

3 with a compound of formula 8:

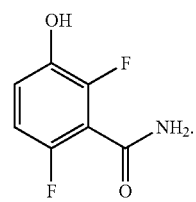

8

In one embodiment the reaction can be carried out at a temperature in the range of from about 0° C. to about 50° C. In one embodiment, the reaction can be carried out in a polar solvent, such as, for example, a solvent that comprises THF, DMF, acetylnitrile ACN, or dimethylsulfoxide DMSO. In one embodiment, the reaction can be carried out in in the presence of a suitable base, such as, for example, an amine base (e.g. a hindered amine base like N,N-diisopropyl-N-ethylamine), or an inorganic base (e.g. NaH, KH, NaOH, KOH, $K_2CO_3$, or NaOtBu). In one embodiment the reaction can be carried out at a temperature in the range of about 0° C. to about 30° C. in acetonitrile with $K_2CO_3$ as base.

In one embodiment the invention provides a process for preparing a compound of formula 3:

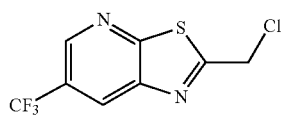

3 by reacting a compound of formula 2:

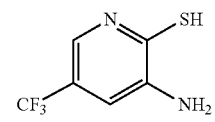

2 with a compound of formula:

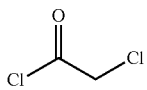

to provide the compound of formula 3. In one embodiment the reaction can be carried out at a temperature in the range of from about 50° C. to about 55° C. In one embodiment the reaction can be carried out at a temperature in the range of from about 45° C. to about 60° C. In one embodiment the reaction can be carried out in a polar solvent. In one embodiment the reaction can be carried out at in a solvent that comprises ethyl acetate, a chlorinated hydrocarbon (e.g. dichloromethane), or an aromatic hydrocarbon (e.g. toluene).

In one embodiment the invention provides a method for preparing a compound of formula 2:

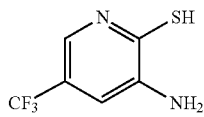

by reducing a corresponding nitro compound of formula 1:

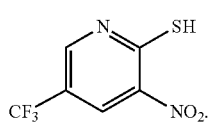

In one embodiment the reduction can be carried out at a temperature in the range of from about 65° C. to about 70° C. In one embodiment the reduction can be carried out at a temperature in the range of from about 60° C. to about 80° C. In one embodiment the reduction can be carried out in a polar solvent. In one embodiment the reduction can be carried out in a solvent that comprises ethyl acetate. In one embodiment the reduction can be carried out in the presence of a suitable reducing agent (e.g. iron/acetic acid, or zinc/ammonium chloride).

In one embodiment the invention provides a process for preparing a compound of formula 1:

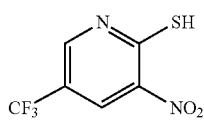

by reacting a compound of formula:

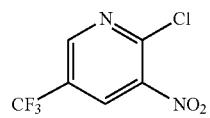

with a compound of formula:

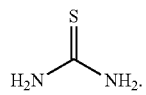

In one embodiment the reaction can be carried out at a temperature in the range of from about 50° C. to about 55° C. In one embodiment the reaction can be carried out at a temperature in the range of from about 40° C. to about 60° C. In one embodiment the reaction can be carried out in a protic solvent. In one embodiment the reaction can be carried out in a solvent that comprises methanol, isopropyl alcohol or ethanol.

In one embodiment the invention provides a method for preparing a compound of formula 7

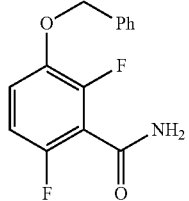

by converting a compound of formula 6:

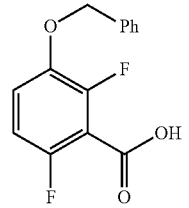

to the compound of formula 7. In one embodiment the conversion can be carried out at a temperature in the range of from about 25° C. to about 30° C. In one embodiment the conversion can be carried out at a temperature in the range of from about 20° C. to about 40° C. In one embodiment the conversion can be carried out in a polar solvent. In one embodiment the conversion can be carried out in a solvent that comprises DMF or THF. In one embodiment the conversion can be carried out in the presence of a suitable base (e.g. aqueous ammonia).

In one embodiment the invention provides a method for preparing a compound of formula 6:

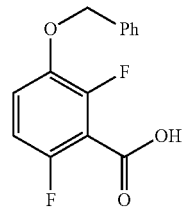

by carboxylating a compound of formula 5:

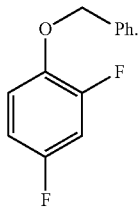

In one embodiment the carboxylation can be carried out at a temperature in the range of from about −75° C. to about 0° C. In one embodiment the carboxylation can be carried out at a temperature in the range of from about −80° C. to about 0° C. In one embodiment the carboxylation can be carried out in a polar solvent. In one embodiment the carboxylation can be carried out in a solvent that comprises an ether (e.g. THF, diethyl ether or methyl tert-butyl ether MTBE). In one embodiment the carboxylation can be carried out in the presence of a suitable base (e.g. n-BuLi).

In one embodiment the invention provides a method for preparing a compound of formula 5:

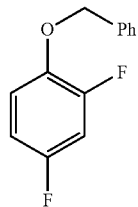

by benzylating a phenol of formula 4:

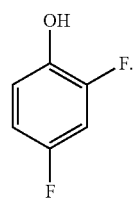

In one embodiment the benzylation reaction can be carried out at a temperature in the range of from about 55° C. to about 60° C. In one embodiment the benzylation reaction can be carried out at a temperature in the range of from about 40° C. to about 65° C. In one embodiment the benzylation reaction can be carried out in a polar solvent (e.g. a solvent that comprises acetone or acetonitrile), or in a protic solvent (e.g. a solvent that comprises methanol or ethanol). In one embodiment the benzylation reaction can be carried out in the presence of a suitable base (e.g. potassium carbonate or sodium carbonate).

The invention will now be illustrated by the following non-limiting Examples.

EXAMPLES

Example 1. 2,6-Difluoro-3-hydroxybenzamide (formula 8)

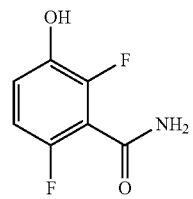

1-(Benzyloxy)-2,4-difluorobenzamide (9.5 kg, 36.1 mol) in 95 L methanol, using 5%-Pd/C (1.43 kg) in methanol at 35-40° C. under Hydrogen pressure (5.0 kg/cm$^2$) in a 250 L SSR reactor. It was observed that the reaction was progressed very slowly and taken more time for reaction completion (IPC:SM:NMT 1.0%). Suspecting the slowness of reaction might be due to the catalyst got deactivated during the reaction after 80% of conversion of starting material. Hence a deviation was taken and fresh lot of 5%-Pd/C (1.43 kg) was added 42.5 hours later after filtration. The reaction was the found to be completed almost immediately. The product was isolated by using methylene dichloride and dried in vacuum oven at 50-55° C. to give 5.4 kg of 2,6-difluoro-3-hydroxybenzamide in 89.0% yield.

1-Benzyloxy)-2,4-difluorobenzamide as used in the preceding example was prepared as described below.

a. Preparation of 1-(Benzyloxy)-2,4-difluorobenzene

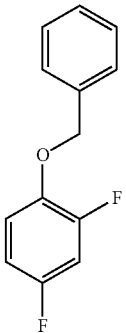

To a 250 L SS Reactor, was charged 2, 4-difluorophenol 8.0 kg, 46.2 mol), benzyl bromide (10.6 kg, 49.9 mol), potassium carbonate (10.2 kg, 73.8 mol) and acetone (48 L) at 50-60° C. The contents were stirred for 1 hour at 55-60° C. The reaction completion was monitored by HPLC. After completion of the reaction, distilled the acetone was removed under vacuum below 50° C. and cooled to 25-30° C. Water (5.0 L) was added slowly at 25-30° C. and further cooled to 0-10° C. The contents were stirred for 1 hour and the solid was filtered and dried to give a crude solid. The crude product was washed with water (96 L) and 10% isopropyl alcohol: water mixture (56 L) at 25-30° C. and dried at 30-35° C. under reduced pressure for 8 hours to give pure product as white solid (12.1 kg, 89% yield). $^1$H NMR (300 MHz, DMSO-d$_6$) δ: 7.23-7.47 (m, 7H), 6.97-7.05 (m, 1H), 5.16 (s, 2H).

b. Preparation of 3-(Benzyloxy)-2,6-difluorobenzoicacid (formula 6)

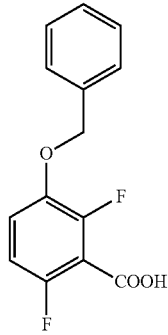

To a 1.6 KL SS Reactor, was charged THF (175.5 L) and diisopropyl amine (7.0 kg, 69.2 mol) under nitrogen atmosphere. The reaction mixture was cooled to 0 to −10° C., then n-BuLi (1.6 M solution in hexane) (27 kg, 43.2 mol) was added slowly and stirred the mixture for 4 hour at 0 to −10° C. The contents were cooled to −55 to −75° C., then 1-(benzyloxy)-2,4-difluorobenzene (11.7 kg, 53.1 mol) solution in THF (175.5 L) was added slowly drop wise at −60 to −75° C. and stirred for 1 hour. Dry $CO_2$ gas was purged into the reaction mixture for 4.0 hours at −55 to −75° C. The reaction completion was monitored by TLC. After reaction completion, the temperature of the reaction mixture was raised to 0-20° C. and the pH was adjusted to 0-2 with 6N HCl solution (66.4 L) and water (128.7 L) was added. The layers separated and aqueous layer was extracted with MDC. The organic layers combined and concentrated at below 50° C. under reduced pressure to give crude solid and checked for HPLC purity. The obtained crude was further purified by using base-acid treatment with 10% NaOH solution and followed by washing with 10% ethyl acetate:cyclohexane mixture (46.8 L) and filtered. The product was dried at 60-65° C. for 8 hours to give a pure product as white solid. (10.4 kg, 73.8% yield). $^1$H NMR (300 MHz, DMSO-$d_6$) δ: 13.98 (bs, 1H), 7.33-7.47 (m, 6H), 7.10-716 (m, 1H), 5.20 (s, 2H). MS: 265.12 (M+1).

c. Preparation of 1-(Benzyloxy)-2,4-difluorobenzamide (formula 7)

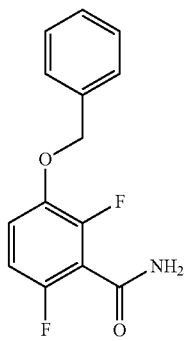

To a 250 L AGLR, was charged 3-(benzyloxy)-2,6-difluorobenzoic acid (10.3 kg, 39 mol), DMF (1.03 L) and dry THF (30.9 L) under nitrogen atmosphere. Thionyl chloride (6.95 kg, 4.5 mol) was added slowly at 25-30° C. The reaction mixture was stirred for 4 hours at 25-30° C. The reaction completion was monitored by TLC. After reaction completion, the reaction mixture was quenched in aqueous ammonia solution (17%, 103 L) at below 20° C. and stirred for 2 hours. The THF solvent was distilled completely at below 50° C. under reduced pressure. The precipitated solid was filtered and washed with water (72.1 L) to give a crude product as a solid. The crude product was purified by slurry-washing with 10% ethyl acetate:cyclohexane (41.2 L), filtered and dried at 60-65° C. for 8 hours to give pure product as white solid. (9.51 kg, 92.7% yield). $^1$H NMR (300 MHz, DMSO-$d_6$) δ: 8.14 (bs, 1H), 7.85 (bs, 1H), 7.25-7.47 (m, 6H), 7.03-7.09 (m, 1H), 5.15 (s, 2H).

Example 2. 2-(Chloromethyl)-6-(trifluoromethyl)[1,3]thiazolo[5,4-b]pyridine (formula 3)

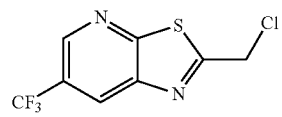

To a 250 L GLR, was charged 3-amino-2-thio-5-(trifluoromethyl)pyridine (6.49 kg, 25.7 mol) and ethyl acetate (97.4 L) at 25-30° C. The contents were cooled to 10-15° C. and chloroacetyl chloride (7.6 kg, 67.3 mol) was added slowly to the reaction mixture at 10-15° C. The reaction mixture was stirred for 15 hours at 50-55° C. The reaction completion was monitored by HPLC. After reaction completion, water (32.5 L) was added slowly at 25-30° C. The organic layer was separated and washed with 8% sodium bicarbonate (20.5 L), water (19.5 L) and then sat. NaCl (23 L) solution. The organic layer was concentrated and co-distilled with isopropyl alcohol. The product was washed with isopropyl alcohol (22.75 L) at 5-10° C. filtered and dried to give the final product as a brown solid (6.28 kg, 74.4% yield). $^1$H NMR (300 MHz, $CDCl_3$) δ: 8.88 (s, 1H), 8.47-8.48 (s, 1H), 4.96 (s, 2H). MS: 252.99 (M+1).

3-Amino-2-thio-5-(trifluoromethyl) pyridine as used in the preceding example was prepared as described below.

a. Preparation of 3-Nitro-2-thio-5-(trifluoromethyl)pyridine

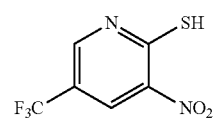 [SMILES: O=[N+]([O-])c1cc(C(F)(F)F)cnc1S]

To 250 L AGLR, was charged 2-chloro-3-nitro-5-(trifluoromethyl)pyridine (13 kg, 57.4 mol), methanol (78 L) and thiourea (4.81 kg, 63.2 mol) at 25-30° C. The reaction mixture was stirred using a motor driven agitator for 4 hours at 50-55° C. The reaction completion was monitored by HPLC. After completion, methanol from the reaction mixture was distilled out completely under reduced pressure at below 45° C. Water (65.0 L) was added to the reaction mixture at 25-30° C., followed by aqueous NaOH solution (45.9%, 20.5 L) added slowly at 25-30° C. The aqueous layer was washed with toluene (3×19.5 L) and the product was precipitated by adjusting the pH to 1-2 with 6N HCl solution (23.5 L) at 0-5° C. The precipitated product was collected, filtered and dried to give the product as brown solid in good yield. The crude product was used without further purification in the next step. $^1$H NMR (300 MHz, DMSO-d$_6$) δ: 14.99 (bs, 1H,), 8.56-8.57 (s, 1H), 8.37 (s, 1H). MS: 223.13 (M−1).

b. Preparation of 3-Amino-2-thio-5-(trifluoromethyl)pyridine

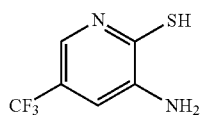

To a 250 L AGLR, was charged 3-nitro-2-thio-5-(trifluoromethyl) pyridine (as obtained crude from Example 3a), iron powder (8.71 kg, 156 mol), ethyl acetate (26 L) and water (26 mL). Acetic acid (26 L) was then added slowly at 25-30° C. The reaction mixture was stirred for 1 hour at 65-70° C. The reaction completion was monitored by HPLC. After reaction completion, the reaction mixture was cooled to 25-30° C. and ethyl acetate (39.0 L) and water (39.0 L) was added. The reaction mass was filtered through a Hyflo bed and the layers were separated. The combined organic layer was washed with 7% sodium bicarbonate (40 L), water (39 L) and sat. NaCl solution and the layers were separated. The organic layer was concentrated and the product was precipitated by using methylene dichloride (52 L) at 5-10° C. The solid isolated was filtered and dried to give final product as brown solid. (65.0 kg g, 58.3% yield from 2-chloro-3-nitro-5-(trifluoromethyl) pyridine, Example 2a). $^1$H NMR (300 MHz, DMSO-d$_6$) δ: 13.85 (bs, 1H), 7.41 (s, 1H), 6.82-6.83 (s, 1H), 6.16 (s, 2H). MS: 195.08 (M+1).

Example 3. 2,6-Difluoro-3-((6-(trifluoromethyl) thiazolo[5,4-b]pyridin-2-yl)methoxy)benzamide (TXA707, Formula 9)

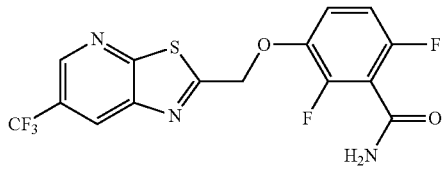

2,6-Difluoro-3-hydroxybenzamide (3.56 kg, 20.6 mol), potassium carbonate (3.41 kg, 24.7 mol) and 2-(chloromethyl)-6-(trifluoromethyl)[1,3]thiazolo[5,4-b]pyridine (6.23 kg. 24.7 mol.) and a catalytic amount of TBAB (1.324 kg) in acetonitrile (35.6 L) under nitrogen atmosphere were added to a 100 L AGLR. The reaction mixture was stirred for 30 hours at 25-30° C. The reaction mixture was quenched with 1N HCl and the pH adjusted to 7.0 to 7.5. The precipitated solid was filtered and washed with water to give a brown solid. The crude solid obtained was purified with water (81.0 L) and dried for 18 hours at 60-65° C. to provide N-(2,6-difluoro-3-((6-(trifluoromethyl)thiazolo[5,4-b]pyridin-2-yl)methoxy)benzoyl)-1-methyl-piperidine-4-carboxamide (7.35 kg 91.8% yield). $^1$H NMR (300 MHz, DMSO-d$_6$) δ: 9.03-9.04 (s, 1H), 8.88-8.89 (s, 1H), 7.35-7.43 (m, 1H), 7.06-7.13 (m, 1H), 5.74 (s, 2H). MS: 390.10 (M+1).

Example 4. N-(2,6-Difluoro-3-((6-(trifluoromethyl) thiazolo[5,4-b]pyridin-2-yl)methoxy)benzoyl)-1-methylpiperidine-4-carboxamide (TXA709, Formula 10)

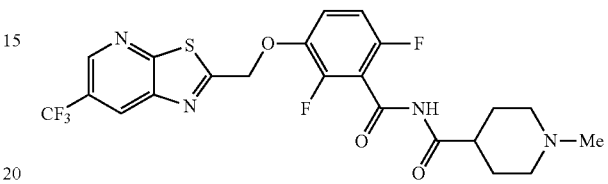

TXA707 (7.1 kg, 18.2 mol), N-methylpiperidine-4-carboxylic acid hydrochloride (4.92 kg, 27.4 mol) together with EDC hydrochloride (6.99 kg, 36.5 mol) and DMAP (11.15 kg, 91.3 mol) in 142 L of methylene chloride were stirred at 35-40° C. for 2 hours. The reaction was quenched with water (213.0 L), distill-off the methylene chloride, followed by filtration and washing with water (71.0 L) and dried under vacuum to provide the desired product (8.5 kg, 76.4% yield), 1-H NMR (300 MHz, CDCl$_3$) δ: 8.58 (s, 1H), 8.31 (broad s, 1H), 8.24 (s, 1H), 7.24-7.14 (m, 1H), 6.94-6.87 (m, 1H), 5.50 (s, 2H), 2.94-2.80 (m, 3H), 2.28 (s, 3H), 2.10-1.74 (m, 6H). $^{13}$C NMR (100 MHz, DMSO-d$_6$) δ 174.9, 171.1, 161.2, 160.3, 153.5, 151.1, 149.1, 146.6, 144.5, 143.8, 141.8, 141.7, 127.8, 125.0, 124.1, 123.8, 123.5, 123.2, 122.3, 129.6, 117.6, 117.5, 115.9, 117.7, 115.6, 111.4, 111.1, 69.1, 54.8, 54.4, 45.9, 41.9, 27.6. HRMS calculated for C$_{22}$H$_{19}$F$_5$N$_4$O$_3$S (M+H)+, 515.1171; found, 515.1181.

Example 5. N-(2,6-Difluoro-3-((6-(trifluoromethyl) thiazolo[5,4-b]pyridin-2-yl)methoxy)benzoyl)-1-methylpiperidine-4-carboxamide Mesylate (TXA709 mesylate, Formula 11)

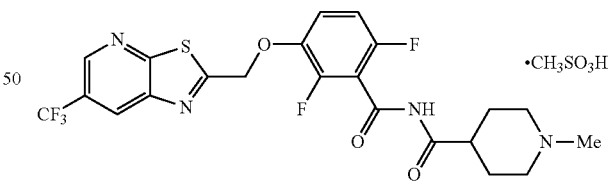

TXA709 (8.77 kg) was dissolved in acetone (213 L) and methane sulfonic acid (1.93 kg) was added at 40-50° C. The mixture was stirred for 3 hours. The resulting precipitate was collected as a crystalline solid. Further purification was accomplished by using 10% methanol in acetone (700 ml/100 g; repeated 2×) and drying at 55-60° C. under vacuum. The salt was sieved in 20 mesh for uniformity. $^1$H NMR (300 MHz, DMSO-d$_6$) δ: 11.74 (bs, 1H), 9.07 (s, 1H), 8.95 (s, 1H), 7.50-7.58 (m, 1H), 7.17-7.24 (m, 1H), 5.81 (s, 2H), 3.45-3.50 (d, 2H), 2.91-3.02 (m, 2H), 2.77-2.84 (d, 4H), 2.31 (s, 3H), 2.04-2.08 (d, 2H), 1.65-1.77 (m, 2H). MS: 515.08 (M+1).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A process for preparing TXA709:

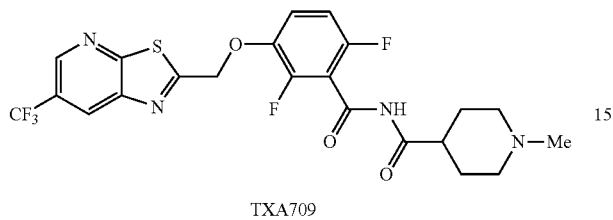

TXA709 comprising converting an amide of formula 9:

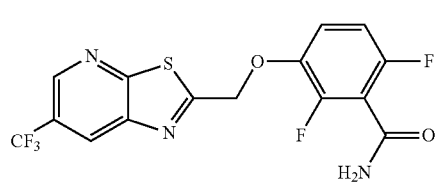

to TXA709 on a commercial scale.

2. The process of claim 1 further comprising preparing the compound of formula 9:

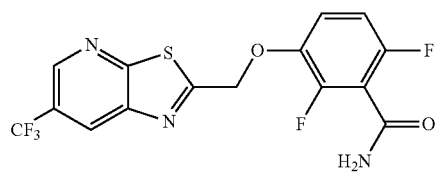

by reacting a compound of formula 3:

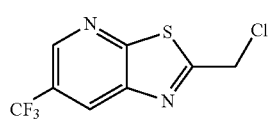

with a compound of formula 8:

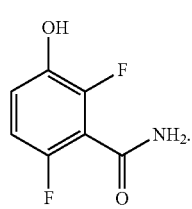

3. The process of claim 2 further comprising preparing the compound of formula 3 by reacting a compound of formula 2:

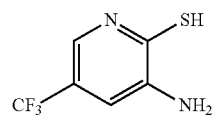

with a compound of formula:

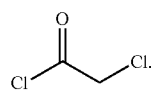

4. The process of claim 3 further comprising preparing the compound of formula 2 by reducing a nitro compound of formula 1:

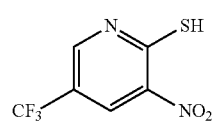

to provide the compound of formula 2.

5. The process of claim 4 further comprising preparing the compound of formula 1 by reacting a compound of formula:

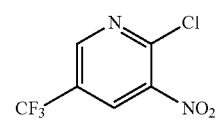 [SMILES: O=[N+]([O-])c1cc(C(F)(F)F)cnc1Cl]

with a compound of formula:

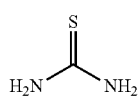

to provide the compound of formula 1.

6. The process of claim 2, further comprising preparing the compound of formula 8 by converting a compound of formula 7:

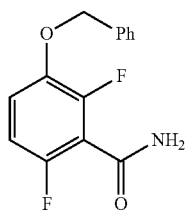

to the compound of formula 8.

7. The process of claim 6 further comprising preparing the compound of formula 7 by converting a compound of formula 6:

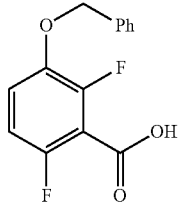

to the compound of formula 7.

8. The process of claim 7 further comprising preparing the compound of formula 6 by carboxylating a compound of formula 5:

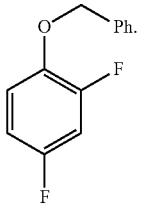

9. The process of claim 8 further comprising preparing the compound of formula 5 by benzylating a phenol of formula 4:

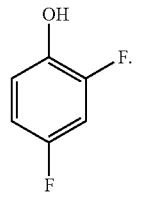

10. A process for preparing a compound of formula 9:

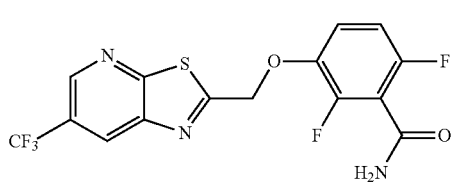

comprising reacting a compound of formula 3:

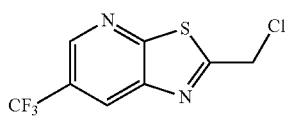

with a compound of formula 8:

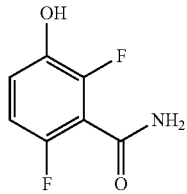

to provide the compound of formula 9 on a commercial scale.

11. The process of claim 10, which is carried out at a temperature in the range of about 0° C. to about 30° C. in acetonitrile with $K_2CO_3$ as base.

12. A process for preparing a compound of formula 8:

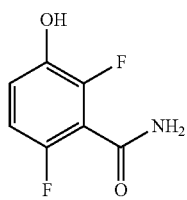

comprising converting a compound of formula 7:

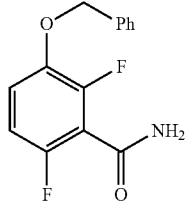

to the compound of formula 8.

13. The process of claim 12 wherein the compound of formula 7 is converted to the compound of formula 8 by hydrogenation.

14. The process of claim 12 wherein the compound of formula 7 is converted to the compound of formula 8 by hydrogenation using palladium on carbon as a catalyst.

15. The process of claim 12, wherein the compound of formula 7 is converted to the compound of formula 8 in the presence of a non-polar solvent.

16. The process of claim 12, wherein the compound of formula 7 is converted to the compound of formula 8 at a temperature in the range from about −78° C. to about 65° C.

* * * * *